United States Patent [19]
Treppendahl et al.

[11] Patent Number: 5,935,987
[45] Date of Patent: Aug. 10, 1999

[54] TRANSDERMAL DELIVERY OF 3,4-DIARYLCHROMANS

[75] Inventors: Svend Treppendahl, Virum; Klaus Snej Jensen, Frederiksberg C; Scott E. McGraw, Stenløse; Helle Weibel, Hillerød, all of Denmark

[73] Assignee: Novo Nordisk A/S, Bagvaerd, Denmark

[21] Appl. No.: 08/972,664

[22] Filed: Nov. 18, 1997

Related U.S. Application Data

[63] Continuation of application No. 08/852,714, May 7, 1997
[60] Provisional application No. 60/019,009, Jun. 3, 1996.

[30] Foreign Application Priority Data

May 8, 1996 [DK] Denmark .................................. 0552/96
Nov. 10, 1997 [DK] Denmark .................................. 1278/97

[51] Int. Cl.$^6$ .......................... A61K 31/35; A61K 31/40; A61F 13/02; C07D 405/12
[52] U.S. Cl. .......................... 514/422; 514/456; 548/525; 548/556; 604/306; 604/307
[58] Field of Search ..................................... 514/456, 422; 548/525, 556; 604/306, 307

[56] References Cited

U.S. PATENT DOCUMENTS 5,147,339  9/1992  Sundstrom ............................... 604/307
5,280,040  1/1994  Labroo et al. ........................... 514/422

*Primary Examiner*—Johann Richter
*Assistant Examiner*—Jane C. Osweckí
*Attorney, Agent, or Firm*—Steve T. Zelson; Elias J. Lambris; Carol E. Rozek

[57] ABSTRACT

Therapeutically effective amounts of a 3,4-diarylchroman can be administered transdermally by incorporation of the 3,4-diarylchroman in a matrix or liquid reservoir patch suitable for transdermal delivery, which matrix or liquid reservoir patch optionally contains hydrophobic and/or hydrophilic vehicle(s).

7 Claims, No Drawings

TRANSDERMAL DELIVERY OF 3,4-DIARYLCHROMANS

CROSS-REFERENCE TO RELATED APPLICATIONS

This application is a continuation-in-part of application Ser. No. 08/852,714 filed on May 7, 1997 and claims priority under 35 U.S.C. 119 of US provisional application Ser. No. 60/019,009 filed on Jun. 3, 1996 and Danish application Ser. Nos. 1278/97 filed on Nov. 10, 1997 and 0552/96 filed on May 8, 1996, the contents of which are fully incorporated herein by reference.

TECHNICAL FIELD

The present invention relates to a transdermal delivery system comprising a 3,4-diarylchroman. More particularly, this invention relates to a method of enhancing the penetration of a compound selected from a 3,4-diarylchroman, through human and non-human skin and membranes. The invention also relates to a method for reducing or preventing bone loss, for lowering serum cholesterol, inhibiting lipid accumulation in the arterial wall, use as a vasodilator, for the prevention and treatment of atherosclerosis, hyperlipidemia and hypercoagulability, for the treatment of female patients suffering from endometriosis, dysfunctional bleeding, endometrial cancer, polycystic ovarian syndrome, anovulatory bleeding and breast cancer and male patients with gynecomastia, prostate hypertrophy and prostate carcinoma, for inducing endometrial thinning prior to intrauterine surgery, for treating menopausal symptoms, and atrophy of mucous membranes and skin, for the treatment of patients suffering from obesity and Alzheimer's disease. Furthermore, the invention concerns the use of a 3,4-diarylchroman for the preparation of a transdermal delivery system.

BACKGROUND ART

Bone remodeling is the dynamic process whereby skeletal mass and architecture are renewed and maintained. This renewal and maintenance is a balance between bone resorption and bone formation, with the osteoclast and the osteoblast considered the two key participants in the remodeling process. The osteoclast initiates the remodeling cycle by resorbing a cavity in the bone which is subsequently refilled when the osteoblast synthesizes and deposits new bone matrix into the excavation. The activities of osteoclast and osteoblast are regulated by complex interactions between systemic hormones and the local production of growth factors and cytokines at active remodeling sites Imbalances in bone remodeling are associated with such conditions as osteoporosis, Paget's disease, and hyperparathyrodism. Osteoporosis, characterized by a decrease in the skeletal mass, is one of the most common diseases of postmenopausal women and is often the cause of debilitating and painful fractures of the spine, hip and wrist.

Approximately 25% of all postmenopausal women suffer from osteoporosis, and it is generally accepted that the etiology of the disease involves the reduction of circulating estrogens (Komm et al., *Science* 241:81–84, 1988) Komm et al. further report that the proportion of Caucasian women in the United States who are at risk for a hip fracture is 15%, or 247,000 hip fractures per year in women over the age of 45.

The costs of osteoporosis, both personal and financial, are enormous. In 1984, 145,000 in-patient fracture reductions and 107,000 hip arthroplasties and replacements were performed on American women over 65 years of age. Among patients who lived alone prior to hip fracture, 15% to 20% required long-term care as a result of the fracture and one year after the fracture had still not regained their independence. The total financial cost of osteoporosis treatment, including fractures, in the United States in 1986 was 7–10 billion dollars (Peck et al., *Am.J.Med.* 84:275–282,1988).

Bone loss associated with osteoporosis has been arrested by the administration of exogeneous estrogens. To be effective, estrogen therapy must begin within a few years of the onset of menopause, and should continue for 10 to 15 years, according to Thorneycroft (*Am.J.Obstet.Gynecol.* 160:1306.1310m 1989), While there are several different types of estrogens, 17-$\beta$-estradiol is the primary estrogen found naturally occurring in premenopausal women and is often the compound of choice for theraptic use. At the recommended dose, however, there are significant side effects, the most distrubing being the well-established correlation of estrogen therapy with endometrial and brest cancers. The incidence of carcinoma is both dose-dependent and duration-dependent.

3,4-diarylchromans and their salts are useful within human and veterinary medicine for the regulation of bone metabolism. These compounds may be used, for example, in the treatment of patients suffering from bone loss due to osteoporosis (including post-menopausal osteoporosis and glucocorticoid-related osteoporosis), Paget's disease, hyperparathyroidism, hypercalcemia of malignancy and other conditions characterized by excessive rates of bone resorption and/or decreased rates of bone formation.

Avoidance of the cancer risk has been achieved by the concomitant use of a progestogen with estrogen. This combination , however, causes menses to return, which many women find unacceptable. A further disadvantage is that the longterm effects of the progestogen have not been fully determined. Thus, a large population of women require alternatives to hormone replacement therapies that can safely prevent the rapid bone loss that accompanies the menopause.

The formula I compounds are described in U.S. Pat. No. 5,280,040. This patent describes the preparation of these compounds, as well as their use in reducing bone loss. The preparation of pharmaceutical compositions is also described.

Centchroman, which is 3,4-trans-2,2-dimethyl-3-phenyl-4-[4-(2-pyrrolidin-1-yl)ethoxy)phenyl]-7-methoxychroman, is a non-steroidal compound known to have antiestrogenic activity. It is in use in India as an oral contraceptive (see, for example, Salman et al U.S. Pat. No. 4,447,622; Singh et al., Acta Endocrinal (Copenh) 126 (1992), 444–450; Grubb, Curr Opin Obstet Gynecol 3(1991), 491–495; Sankaran et al., Contraception 9(1974), 279–289; Indian Patent Specification No. 129187). Centchroman has also been investigated as an anti-cancer agent for treatment of advanced breast cancer (Misra et al., Int J Cancer 43 (1989), 781–783). Recently, centchroman as a racemate has been found as a potent cholesterol lowering pharmaceutical agent expressed by a significant decrease of the serum concentrations (S. D. Bain et al., J Min Bon Res 9 (1994), S 394).

Levormeloxifene, (−)-3R,4R-trans-7-methoxy-2,2-dimethyl-3-phenyl-4-{4-[2-(pyrrolidin-1-yl)ethoxy] phenyl}chromane, is a particular preferred compound from this series of 3,4-diarylchromans. Levormeloxifene may be used in human and veterinary medicine for the regulation of bone metabolism. It may be used, for example, in the treatment of patients suffering from bone loss due to osteoporosis (including post-menopausal osteoporosis and glucocorticoid-related osteoporosis), Paget's disease, hyperparathyroidism, hypercalcemia of malignancy and other conditions characterized by excessive rates of bone resorption and/or decreased rates of bone formation.

The 3,4-diarylchromans are prepared according to known methods, such as those disclosed in U.S. Pat. No. 3,340,276 to Carney et al., U.S. Pat. No. 3,822,287 to Bolger, and Ray et al., J Med Chem 19 (1976), 276–279, the contents of which are incorporated herein by reference. Conversion of the cis isomer to the trans configuration by means of an organometallic base-catalyzed rearrangement is disclosed in U.S. Pat. No. 3,822,287. The optically active d- and l-enantiomers may be prepared as disclosed by Salman et al. in U.S. Pat. No. 4,447,622 (incorporated herein by reference) by forming an optically active acid salt which is subjected to alkaline hydrolysis to produce the desired enantiomer. The resolution of (+/−)-3,4-trans-7-methoxy-2,2-dimethyl-3-phenyl-4-{4-[2-(pyrrolidin-1-yl)ethoxy] phenyl}chromane in its optical antipodes is described in U.S. Pat. No. 4,447,622 incorporated herein by reference. Example 1 of U.S. Pat. No. 4,447,622 describes the preparation of the minus enantiomer, shown by formula II:

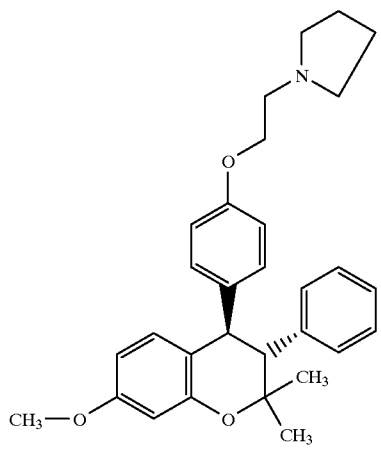

(II)

(In this specification, the compound of formula II is referred to as levormeloxifene.)

In example 2 of U.S. Pat. No. 4,447,622, levormeloxifene is obtained as the free base and the hydrochloride salt. The compounds of formula I may be administered as pharmaceutically acceptable salts. A particularly useful pharmaceutically acceptable salt of levormeloxifene is the hydrogen fumarate salt (in this specification, this compound is referred to as levormeloxifene fumarate.). This salt form is prepared by dissolving fumaric acid and (−)-3R,4R-trans-7-methoxy-2,2-dimethyl-3-phenyl-4-{4-[2-(pyrrolidin-1-yl)ethoxy] phenyl}chromane in a common solvent such as e.g. methanol, and crystallizing the resulting salt from the solution.

U.S. Pat. No. 5,280,040 and U.S. Pat. No. 5,464,862 discloses a class of 3,4-diarylchromans and their salts useful for reducing bone loss.

The free base has a very poor solubility in water and the hydrochloride salt has some pharmaceutically undesirable properties. The hydrochloride salt is hygroscopic, it is quite heavy soluble in water and it forms a solid gel in aqueous suspension.

For commercial use it is important to have a physiologically acceptable salt with good stability, non-hygroscopicity, good bioavailability, good handling properties, and a reproducible crystalline form.

The transdermal route for delivery of drugs provides many advantages such as noninvasive drug delivery, no first pass effect, lower dose and better compliance for patients with dosing problems as to conventional dosing forms, i.e. tablets or capsules.

Transdermal systems for delivering a wide variety of drugs or other agents are described in i.a. U.S. Pat. No. 4,978,532 and in PCT publication WO 91/09592.

Drugs can be delivered into the systemic circulation via the human skin membrane with low daily doses because first pass hepatic metabolism is avoided (Todd P. A. & Goa K. L., Drugs 40(4): p. 583–607 (1990)). This may be convenient because low-dose forms may avoid some of the side effects of higher dose oral therapy.

SUMMARY OF THE INVENTION

It has now surprisingly been found that therapeutically effective amounts of a 3,4-diarylchroman can be administered transdermally by incorporation of the 3,4-diarylchroman, preferably levomeloxifene, in a matrix or liquid reservoir patch suitable for transdermal delivery, which matrix or liquid reservoir patch optionally contains hydrophobic and/or hydrophilic vehicle(s).

The present transdermal delivery system provides therapeutically amounts of 3,4-diarylchromans, preferably levormeloxifene, into the systemic circulation.

DESCRIPTION OF THE INVENTION

The present invention relates to a transdermal delivery system comprising a 3,4-diarylchroman of formula I

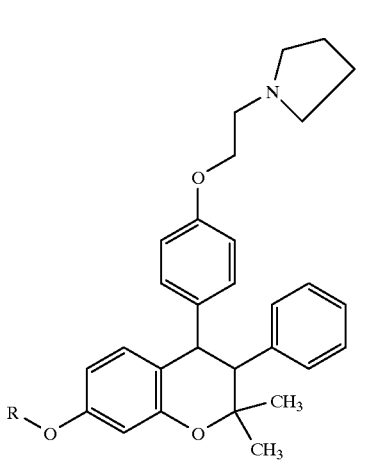

(I)

wherein R is $C_{1-6}$alkyl; or a pharmaceutically acceptable salt thereof.

Within the present invention, the compounds of formula I may be prepared in the form of pharmaceutically acceptable salts, especially acid-addition salts, including salts of organic acids and mineral acids. Examples of such salts include salts of organic acids such as formic acid, fumaric acid, acetic acid, propionic acid, glycolic acid, lactic acid, pyruvic acid, oxalic acid, succinic acid, malic acid, maleic acid tartaric acid, citric acid, benzoic acid, salicylic acid, besylate, citrate, sodium, potassium, calcium, zinc, magnesium, meglumine, acetate, benzoate, fumarate, phosphate, malate, maleate, mandelate, mesylate, lactate, salicylate, sulphate, tartrate, succinate, TFA and the like.

Suitable inorganic acid-addition salts include salts of hydrochloric, hydrobromic, sulphuric and phosphoric acids as well as hydrate salts and the like. The acid addition salts, including hydrate salts, may be obtained as the direct products of compound synthesis. In the alternative, the free base may be dissolved in a suitable solvent containing the appropriate acid, and the salt isolated by evaporating the solvent or otherwise separating the salt and solvent.

In a further embodiment of the present invention R in the compound of formula I is methyl.

In a still further embodiment of the present invention the compound of formula I is in the trans configuration.

In a further embodiment of the present invention the compound of formula I is 3,4-trans-2,2-dimethyl-3-phenyl-4-[4-(2-pyrrolidin-1-yl)ethoxy)phenyl]-7-methoxychroman or a salt thereof.

In a still further embodiment of the present invention the compound of formula I is an isolated I-enantiomer or a salt thereof.

In a further embodiment of the present invention the compound of formula I is (−)-3R,4R-trans-7-methoxy-2,2-dimethyl-3-phenyl-4-{4-[2-(pyrrolidin-1-yl)ethoxy] phenyl}chromane or a salt thereof.

In a still further embodiment of the present invention the compound of formula I is in the form of the hydrogen fumarate salt.

In a still further embodiment of the delivery system the 3,4-diarylchroman of formula I is the levormeloxifene hydrogen fumarate salt.

In a further embodiment of the present invention the compound of formula I is in the form of the hydrogen maleate salt.

In a still further embodiment the delivery system further comprises ionpairs of a 3,4-diarylchroman of formula I and one or more organic acid(s). Ionpairs may be formed between the nitrogen atom of the 3,4-diarylchroman of formula I and a suitable organic acid, e.g. alkylsulphonic acids, dehydrocholic acids, salicylic or oleic acid.

In a further embodiment the delivery system further comprises one or more hydrophobic or hydrophilic vehicles, preferably saturated and unsaturated fatty acids, preferably $C_{14}$–$C_{22}$-acids, more preferably $C_{18}$-acids, and esters thereof, propylene glycol, alfa bisabolal, ethanol, cineol hydroxy propyl-beta-cyclodextrin, dimethylsulfoxid, decylmethylsulfoxid, azone, 2-pyrrolidon, glycerol, polyethylene glycol 400, dimethylformamid, N-methyl-2-pyrrolidone, bisabolol (6-methyl-2-(4-methyl-3-cyclohexen-1-yl)-5-hepten-2-ol), cineol (1,3,3-trimethyl-2-oxabicyclo[2.2.2]octane), hydroxypropyl-b-cyclodextrin (HPCD) or decylmethylsulfoxid (DMS) or mixtures thereof. More preferably acetic acid solution, oleic acid in propylene glycol or ethanol in acetic acid solution or 2-pyrrolidon in acetic acid solution.

In a still further embodiment of the delivery system, the one or more hydrophobic and/or hydrophilic vehicle(s) and a 3,4-diarylchroman of formula I are dispersed in a matrix patch or liquid reservoir patch, preferably a matrix.

The size of a transdermal patch or pad may have any suitable size, which should to be determined by the skilled person. In a particular embodiment the transdermal patch or pad have a size of from about 1 $cm^2$ to about 200 $cm^2$, such as from about 5 $cm^2$ to about 100 $cm^2$, from about 10 $cm^2$ to about 80 $cm^2$, from about 40 $cm^2$ to about 60 $cm^2$, from about 1 $cm^2$ to about 10 $cm^2$, from about 10 $cm^2$ to about 40 $cm^2$, from about 40 $cm^2$ to about 80 $cm^2$, from about 80 $cm^2$ to about 100 $cm^2$ or from about 100 $cm^2$ to about 200 $cm^2$, e.g. about 50 $cm^2$.

The transdermal delivery system, e.g. the matrix patch or liquid reservoir patch, may optionally be in combination with an adhesive in order to keep the 3,4-diarylchroman of formula I in close contact with mammalian tissue, preferably human skin. Such adhesive may be any adhesive which will keep the patch in its place without seriously damaging the tissue. The skilled person may use any preferred adhesive such as a hydrophilic polymer.

In a further embodiment of the delivery system said 3,4-diarylchroman of formula I is delivered to a patient, e.g. a mammal, such as a human, in an amount of from about 0.0001 mg to about 10 mg per day.

The present invention also relates to a method of enhancing the penetration of a compound selected from a 3,4-diarylchroman of formula I or a pharmaceutically acceptable salt thereof, through human and non-human skin and membranes comprising the use of one or more hydrophobic and/or hydrophilic vehicle(s). In one embodiment there may be used hydrophobic vehicle(s). In another embodiment there may be used hydrophilic vehicle(s). In a further embodiment there may be used a mixture of hydrophilic and hydrophobic vehicle(s).

The delivery system according to the present invention is useful in human and veterinary medicine for the regulation of bone metabolism. The present invention provides a delivery system for preventing or reducing bone loss in a mammal in need of such treatment, comprising transdermally administering an effective amount of a 3,4-diarylchroman of formula I, or a pharmaceutically acceptable salt thereof. 3,4-diarylchromans of formula I, such as levormeloxifene fumarate may be used, for example, in the treatment of patients suffering from bone loss due to osteoporosis (including post-menopausal osteoporosis and glucocorticoid-related osteoporosis), Paget's disease, hyperparathyroidism, hypercalcemia of malignancy and other conditions characterized by excessive rates of bone resorption and/or decreased rates of bone formation or in patients susceptible to bone loss. Furthermore, the compound of formula I has effects on the cardiovascular system where it lowers serum cholesterol, inhibits lipid accumulation in the arterial wall, acts as a vasodilator and interferes with the coagulation process, wherefore it may be used for the prevention and treatment of, for example, atherosclerosis, hyperlipidemia and hypercoagulability. It may also be used, for example, in the treatment of female patients suffering from endometriosis, dysfunctional bleeding, endometrial cancer, polycystic ovarian syndrome, anovulatory bleeding and breast cancer and male patients with gynecomastia, prostate hypertrophy and prostate carcinoma. It may also be used to induce endometrial thinning prior to intrauterine surgery. Furthermore, it may be used, for example, to treat menopausal symptoms, and atrophy of mucous membranes and skin. The compound may be used, for example, in the treatment of patients suffering from obesity and Alzheimer's disease.

Moreover, the present invention relates to a method for preventing or reducing bone loss, bone loss due to osteoporosis (including post-menopausal osteoporosis and glucocorticoid-related osteoporosis), Paget's disease, hyperparathyroidism, hypercalcemia of malignancy and other conditions characterized by excessive rates of bone resorption and/or decreased rates of bone formation, for lowering serum cholesterol, inhibiting lipid accumulation in the arterial wall, use as a vasodilator, for the prevention and treatment of, for example, atherosclerosis, hyperlipidemia and hypercoagulability, for example, for the treatment of female patients suffering from endometriosis, dysfunctional bleeding, endometrial cancer, polycystic ovarian syndrome, anovulatory bleeding and breast cancer and male patients with gynecomastia, prostate hypertrophy and prostate carcinoma, for inducing endometrial thinning prior to intrauterine surgery, for treating menopausal symptoms, and atrophy of mucous membranes and skin, for the treatment of patients suffering from obesity and Alzheimer's disease, comprising transdermally administering a therapeutically effective amount of a 3,4-diarylchroman of formula I, or a pharmaceutically acceptable salt thereof to a mammal in need of such treatment.

Use of a 3,4-diarylchroman of formula I (I)

wherein R is $C_{1-6}$alkyl; or a pharmaceutically acceptable salt thereof, for the preparation of a transdermal delivery system for reducing or preventing bone loss, for lowering serum cholesterol, inhibiting lipid accumulation in the arterial wall, use as a vasodilator, for the prevention and treatment of atherosderosis, hyperlipidemia and hypercoagulability, for the treatment of female patients suffering from endometriosis, dysfunctional bleeding, endometrial cancer, polycystic ovarian syndrome, anovulatory bleeding and breast cancer and male patients with gynecomastia, prostate hypertrophy and prostate carcinoma, for inducing endometrial thinning prior to intrauterine surgery, for treating menopausal symptoms, and atrophy of mucous membranes and skin, and for the treatment of patients suffering from obesity and Alzheimer's disease.

By the term "therapeutically effective amount" it is understood that such an amount is sufficient to provide the desired result, that is, for reducing or preventing bone loss, (cf. diseases or disorders mentioned above).

The therapeutically effective amount should be determined by the skilled artisan, but will usually be in the range of from about 0.00001 mg to about 10 mg per kg. body weight per day.

The daily dosage form of the 3,4-diarylchromans of formula I are from 0.00001–10 mg/kg body weight.

In the above structural formulas and throughout the present specification, the following terms have the indicated meanings:

The lower alkyl moities specified above are intended to include those alkyl moities, preferably with 1–6 carbon atoms, of the designated length in either a linear or branched or cyclic configuration. Examples of linear alkyl are methyl, ethyl, propyl, butyl, pentyl, and hexyl. Examples of branched alkyl are isopropyl, sec-butyl, tert-butyl, isopentyl, and isohexyl. Examples of cyclic alkyl are cyclopropyl, cyclobutyl, cydopentyl and cyclohexyl.

The term "treatment" or "treating" is intended to comprise profylactic treatment.

DETAILED DESCRIPTION OF PREFERRED PATCH EMBODIMENTS

A preferred embodiment of the present invention is predicted to be a microsealed, transdermal levormeloxifene fumarate pad having a backing which is impervious to levormeloxifene fumarate absorption and transport, and a silicon polymer matrix affixed thereto, the silicone polymer matrix being of cross-linked silicone rubber having from about 10 to 200 mm microsealed compartments being formed by in situ cross-linking of the silicone rubber after it is mixed with the solvent system containing the levormeloxifene fumarate and the vehicles which enhances levormeloxifene fumarate transport and dispersion, the levormeloxifene fumarate being diffusible through the biologically acceptable silicon polymer matrix at a therapeutically effective constant rate when the microsealed levormeloxifene fumarate pad is affixed to the skin.

A most preferred embodiment of the present invention is predicted to be a microsealed, transdermal levormeloxifene fumarate delivery device comprising a biologically acceptable silicone polymer matrix and wherein the biologically acceptable silicone polymer matrix has microsealed compartments distributed throughout, said microsealed compartments containing from 6 to 22 weight percent of 10 weight percent levormeloxifene fumarate mixed with lactose in a solvent system comprising vehicle mixture, and from 5 to 15 weight percent of a hydrophobic solvent selected from the group consisting of mineral oil, oils derived from coconut oil or mixtures thereof. Representative coconut oil derivatives include isopropyl palmitate and miglyol oil. The microsealed compartments are formed by in situ cross-linking of the liquid silicone polymer after it is emulsified with the hydrophilic solvent system containing the levormeloxifene fumarate.

Generally speaking, to prepare the transdermal levormeloxifene fumarate pad of the present invention, a saturated solution of a 10 percent levormeloxifene fumarate-lactose mixture is prepared in a suitable hydrophilic vehicle mixture. An excess amount of the levormeloxifene fumarate-lactose mixture is maintained in this preparation to obtain a uniform paste after manual or mechanical mixing for approx. 5–10 min. This uniform paste is added to the silicone elastomer, i.e. MDX 4-4210 elastomer, (Dow Coming, Midland, Mich.) along with the required amount of a hydrophobic solvent or a similar solvent mixture, such as mineral oil, isopropyl palmitate, or a mixture thereof. All of these ingredients are mixed from 5 to 15 min. in a low shear, explosion-proof mixing vessel maintained under vacuum. The polymerizing catalyst is added and mixing is continued under vacuum from about 15 to 30 min. The final mixture is viscous, and is poured, with the aid of mixing equipment, into clean, dry stainless steel plates. In the case of 2×4 cm pads, suitable amounts of the final mixture are poured into 12" by 12" stainless steel plates fitted with a frame of a desired thickness ranging from 5.0 mm to 1.2 mm. A suitable material, such as aluminium foil, is placed on the poured material and top plates having the same dimensions as the bottom plates, but without frames, are pressed to fill the molds with the polymerizing formulation. The molds are secured in place with screws in four comers and placed in an air circulating oven at about 60° C. After two hours, the molds are removed, cooled, and the cured pad material adhering to the aluminium foil is pulled off, cut into suitable size pads, e.g. 2×4 cm with aluminium foil backing. The pads are then stored in air tight containers.

The invention will now be described in more detail. The above embodiments should by no means be construed as limiting the invention.

EXAMPLE 1

The effect of selected formulations on levormeloxifene fumarate permeation through human skin in vitro is illustrated in the following way:

Permeation Procedure

Franz glass diffusion cells were used (Franz, T. J.: Curr. Probl. Dermatol., 1978: 7; 58–68).

Experiments were performed on Caucasian abdominal or breast skin obtained after surgery and kept at −20° C. for not more than ten months. After initial thawing the skin was squeezed between a metal and a glass plate, and after refreezing the skin was dermatomed to a thickness of 0.5 mm.

The human skin membrane was enclosed in the glass chambers with ground faces (diffusing area 0.64 cm$^2$). A clamp was used to keep the chambers together. To assure that the stratum corneum membrane was intact, one ml of 0.05 M phosphate buffer pH 7.4 was applied on the epidermal side of the skin, while the lower part of the skin was in contact with the same medium.

After the skin was allowed to equilibrate at 32° C. for one hour, the capacitance was measured with a Lutron DM 6023 Capacitance meter. Values below 0.055 mF indicated that the stratum corneum was intact. After the capacitance experiment was performed, the phosphate buffer from donor and receptor chamber was removed. The epidermal side of the skin was exposed to ambient laboratory conditions, while the lower part of the skin was in contact with receptor medium, consisting of 0.05 M acetic acid pH 4.0, with or without 5% polysorbate 80, 32° C. Before application of donor phase, the receptor medium was allowed to equilibrate with the skin for one hour.

The donor solutions were made of selected vehicles which were saturated with levormeloxifene fumarate, cf. Table 1. To prepare the donor solutions, levormeloxifene fumarate was added to the vehicles, and after stirring at room temperature for 24 hours, the donor solution was saturated with levormeloxifene fumarate and filtered through a Millipore filter 0.22 µm. Thereafter $^{14}$C-levormeloxifene was added to 1.00 ml of the donor solution to give a final concentration of $^{14}$C-levormeloxifene at 3 mg/ml (1,3 mCi/mi). Thereafter the donor solution was applied on the epidermal side of the skin, and the experiment was performed with occlusion. The concentrations of levormeloxifene fumarate in the donor solutions were determined previously by a HPLC method.

To evaluate the differences in permeability of levormeloxifene fumarate between the skin from the different women, a standard solution containing acetic acid pH 4 saturated with levormeloxifene fumarate was investigated as a donor solution on skin from every woman.

At appropriate intervals, samples were taken from the receptor phase and replaced by fresh receptor solution in order to keep sink-conditions. The amount of levormeloxifene fumarate in the receptor solution was determined using liquid scintillatory counting.

Results

The flux (J), representing the levormeloxifene fumarate permeation rate is given as (see: Scheuplein, R. J. & Blank, I. H.:Physiol. Rev. 1971: 51; 702–747.)

$$J = \frac{dq/dt}{A} \quad [1]$$

in which dq/dt is the steady-state rate of permeation or appearance of solute in the receptor solution (mg/hour), and A is the area of the exposed skin (0.64 cm$^2$). The flux was calculated from equation 1 and the slopes of the linear portions of the plots of dq/dt.

The mean value and the standard deviation were calculated of the flux J of the replicates.

The in vitro data expresses the expected doses deliverable by transdermal patches preferable in a size of 1–200 cm$^2$, preferably in a size of 50 cm$^2$.

Amount delivered per day=J×A

J=flux (mg×cm$^{-2}$×24h$^{-1}$)

A=area of a patch (50 cm$^2$)

The results obtained appears from the following Table 1:

TABLE 1

RESULT OF DIFFUSION CELL MEASUREMENTS

| Donor | Test No | Receptor phase | n | Vehicle | Donor Phase Conc. unmarked mg/ml | Factor unmarked/ marked | Flux ± S.D. mg × cm$^{-2}$ × h$^{-1}$ | Dosage per day mg |
|---|---|---|---|---|---|---|---|---|
| Woman Caucasian 20 years Mammal skin week 19 | 12 | B4 | 6 | B4 | 0.325 | 99.6 | 0.495 ± 0.125 | 0.56 |
| | 13 | B4 + 5% P80 | 6 | B4 | 0.325 | 99.6 | 0.433 ± 0.106 | 0.52 |
| | 14 | B4 | 6 | PG + 10% oleic acid | 116 | 3749 | 1.17 ± 0,545 | 1.40 |
| Frozen 10 months | 15 | B4 | 3 | B4 + 20% ethanol | 1.4 | 399 | 2.00 ± 0.038 | 2.40 |
| Woman Caucasian 47 years week 20 Abdomal skin Frozen 2 weeks | 16 | B4 + 5% P80 | 6 | B4 | 0.32 | 103 | 0.117 ± 0.069 | 0.14 |
| | 17 | B4 + 5% P80 | 6 | B4 + 2% Pyrro | 0.42 | 136 | 0.190 ± 0.165 | 0.23 |
| | 18 | B4 + 5% P80 | 6 | B4 + 30% ehtanol | 3.1 | 995 | 0.302 ± 0.113 | 0.36 |

B4 = Acetic acid 0.05M, pH = 4

TABLE 1-continued

RESULT OF DIFFUSION CELL MEASUREMENTS

| | | | | Donor Phase | | | |
|---|---|---|---|---|---|---|---|
| Donor | Test No | Receptor phase | n | Vehicle | Conc. unmarked mg/ml | Factor unmarked/ marked | Flux ± S.D. mg × cm$^{-2}$ × h$^{-1}$ | Dosage per day mg |

P80 = Polysorbate 80
PG = propylenglycol
Pyrro = 2-Pyrrolidon

EXAMPLE 2

Levormeloxifene fumarate-patch with oleic acid (E)

A 10 percent levormeloxifene fumarate-lactose mixture (55 g) is preferably mixed for about 5 min. with 25.0 g of 10 percent (v/v) oleic acid solution in propylene glycol. A uniform paste of the above mixture was added to 157.5 g of MDX 4-4210 silicone elastomer (Dow Coming, Midland, Mich.). Upon mixing for about 10 min. under initial deaeration, a uniform dispersion was obtained in a low shear mixer. To this dispersion was added 12.5 g of the curing agent for the MDX 4-4210 elastomer and mixing was continued for another 15 min. The final mixture was poured into 12"×12" stainless steel plates with a 5 cm frame to hold the curing material. Aluminium foil (12"×12") was placed into each plate and pressed into the mold with a 12"×12" stainless steel plate. The molds were secured with screws affixed on four corners and placed in an air-circulating oven at about 60° C. for approx. two hours. Upon cooling, the polymer matrix, adhering to the aluminium foil as a backing, was removed from the molds and cut into 1.6×3.2 cm pads which were stored in air tight containers until use.

Levormeloxifene fumarate and maleate was synthesized, purified and crystallized as described in the following examples.

EXAMPLE 3

(−)-3R,4R-trans-7-methoxy-2,2-dimethyl-3-phenyl-4-{4-[2-(pyrrolidin-1-yl)ethoxy]phenyl}chromane, hydrogen fumarate (levormeloxifene fumarate).

To a stirred, 50° C. warm, solution of (+/−)-trans-7-methoxy-2,2-dimethyl-3-phenyl-4-{4-[2-(pyrrolidin-1-yl) ethoxy]phenyl}chromane (1.00 kg, 2.19 mol) in methanol (10 l) was added (+)-ditoluoyltartaric acid (464 g, 1.20 mol). The suspension was stirred at 50° C. until the solution was homogenous.

Formic acid (73 g, 1.59 mol) was added to the solution and the temperature was allowed to drop to 30–40° C. If the crystallization has not started at this point, the solution was seeded, and the temperature was allowed to drop further down to 20° C. The suspension was stirred for two hours at 20° C. and then cooled down to 5–10° C. for two hours and the crystals were collected by filtration. Yield 742 g.

Recrystallization from refluxing methanol (26 l) gave after cooling to 5–10° C. and filtration pure crystals of the levormeloxifene (+)-ditoluoyltartrate salt. Yield 556 g. M.p. 136–138° C. (dec.).

(−)-3R,4R-trans-7-methoxy-2,2-dimethyl-3-phenyl-4-{4-[2-(pyrrolidin-1-yl)ethoxy]phenyl}chromane, (+)-ditoluoyltartrate (500 g) was suspended in a mixture of toluene (2.5 l), water (2 l) and sodium carbonate (157 g) at ambient temperature. The mixture was stirred until the salts were dissolved. The aqueous phase was separated. The toluene phase was washed with water (2 l) and evaporated to an oil. The oil was dissolved in ethanol (1 l) at 40–60° C. and the solution was added to a solution of fumaric acid (69 g, 0.59 mol) in ethanol (2 l). The fumarate salt crystallized readily and the mixture was stirred for an hour at 40–60° C. and then cooled down to 5° C. The title compound was collected by filtration and dried at 50° C. to give 321 g (57%).

M.p. 225° C. (DSC).

$^1$H-NMR (DMSO-d$_6$, TMS): d (ppm): 2.90 (4H,m), 1.75 (4H, m), 3.10 (2H,t), 4.06 (2H,t), 6.69 (2H,d), 7.01 (2H,d), 4.50 (1 H,d), 6.44 (1 H,m), 6.33(1 H, m), 6.38(1 H, m), 3.28(1H,d), 7.31(2H, br.s), 7.20(2H,m), 7.11(1H, m), 1.15 (3H,s), 1.27(3H,s), 3,68(3H, s), 6.53(2H,s) 10.0(2H, s).

MS: 457.2632 (M$^+$ measured), 457.2617 (M$^+$ calculated)

Elemental Analysis: (C$_{30}$H$_{35}$NO$_3$,C$_4$H$_4$O$_4$), Calculated: C:71.18%, H: 6.85%, N: 2.44%, Found: C: 71.23%, N: 7.15%, N: 2.31%

Optical rotation: $[\alpha]^{20}_D$=−153.8° (c=0.5 w/v % in ethanol).

EXAMPLE 4

(−)-3R,4R-trans-7-methoxy-2,2-dimethyl-3-phenyl-4-{4-[2-(pyrrolidin-1-yl)ethoxy]phenyl}chromane, hydrogen maleate (levormeloxifene maleate)

To a stirred, 50° C. warm, solution of (+/−)-trans-7-methoxy-2,2-dimethyl-3-phenyl-4-{4-[2-(pyrrolidin-1-yl) ethoxy]phenyl}chromane (1.00 kg, 2.19 mol) in methanol (10 l) was added (+)-ditoluoyltartaric acid (464 g, 1.20 mol). The suspension was stirred at 50° C. until the solution was homogenous.

Formic acid (73 g, 1.59 mol) was added to the solution and the temperature was allowed to drop to 30–40° C. If the crystallization has not started at this point, the solution was seeded, and the temperature was allowed to drop further down to 20° C. The suspension was stirred for two hours at 20° C. and then cooled down to 5–10° C. for two hours and the crystals were collected by filtration. Yield 742 g.

Recrystallization from refluxing methanol (26 l) gave after cooling to 5–10° C. and filtration pure crystals of the levormeloxifene (+)-ditoluoyltartrate salt. Yield 556 g. M.p. 136–138° C. (dec.).

(−)-3R,4R-trans-7-methoxy-2,2-dimethyl-3-phenyl-4-{4-[2-(pyrrolidin-1-yl)ethoxy]phenyl}chromane, (+)-ditoluoyltartrate (500 g) was suspended in a mixture of toluene (2.5 l), water (2 l) and sodium carbonate (157 g) at ambient temperature. The mixture was stirred until the salts were dissolved. The aqueous phase was separated. The toluene phase was washed with water (2 l) and evaporated to an oil.

A part of the oil (3 g, 0.0066 mole) was dissolved in toluene (60 ml). Maleic acid (0.8 g, 0.0066 mole) was added. The mixture was heated until homogenous. It was stirred over night at ambient temperature. The maleinate salt crystallized readily. The title compound was collected by filtration and dried at 50° C. to give 3 g (80%).

The compound was identified by NMR and elemental analysis.

We claim:

1. A transdermal delivery system comprising a 3,4-diarylchroman of formula I

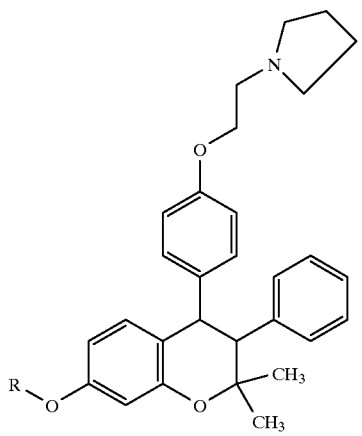

wherein R is $C_{1-6}$alkyl, or a pharmaceutically acceptable salt thereof; a hydrophobic vehicle, and a hydrophilic vehicle or mixtures thereof; wherein the hydrophobic and hydrophilic vehicles and 3,4-diarylchroman are dispersed in a matrix or liquid reservoir patch, and the 3,4-diarylchroman is delivered to a patient in an amount of from about 0.0001 mg to about 10 mg per day.

2. The delivery system according to claim 1 wherein the 3,4-diarylchroman is levormeloxifene.

3. The delivery system according to claim 1 wherein the 3,4-diarylchroman is in the form of the hydrogen fumarate salt.

4. The delivery system of claim 1 being a patch or pad.

5. The delivery system according to claim 4 wherein the patch or pad has a size from about 1 $cm^2$ to about 200 $cm^2$.

6. A method of enhancing the penetration of a compound selected from a 3,4-diarylchroman of formula I or a pharmaceutically acceptable salt thereof, through human and non-human skin and membranes comprising the use of a hydrophobic and/or hydrophilic vehicle(s) or mixtures thereof, wherein said compound of formula I is delivered in an amount of from about 0.00001 mg to about 10 mg per kg body weight per day.

7. A method for reducing or preventing bone loss, for lowering serum cholesterol, inhibiting lipid accumulation in the arterial wall, use as a vasodilator, for the prevention and treatment of atherosclerosis, hyperlipidemia and hypercoagulability, for the treatment of female patients suffering from endometriosis, dysfunctional bleeding, endometrial cancer, polycystic ovarian syndrome, anovulatory bleeding and breast cancer and male patients with gynecomastia, prostate hypertrophy and prostate carcinoma, for inducing endometrial thinning prior to intrauterine surgery, for treating menopausal symptoms, and atrophy of mucous membranes and skin, for the treatment of patients suffering from obesity and Alzheimer's disease, comprising administering to a mammal in need thereof the transdermal delivery system of claim 1.

* * * * *